United States Patent
Dahl et al.

(10) Patent No.: US 9,187,393 B2
(45) Date of Patent: Nov. 17, 2015

(54) PROCESS FOR THE PREPARATION OF DIMETHYL ETHER

(75) Inventors: Per Juul Dahl, Vedbæk (DK); Henrik Otto Stahl, Hørsholm (DK)

(73) Assignee: Haldor Topsoe A/S, Lyngby (DK)

( * ) Notice: Subject to any disclaimer, the term of this patent is extended or adjusted under 35 U.S.C. 154(b) by 377 days.

(21) Appl. No.: 13/576,707

(22) PCT Filed: Jan. 11, 2011

(86) PCT No.: PCT/EP2011/000071
§ 371 (c)(1),
(2), (4) Date: Aug. 2, 2012

(87) PCT Pub. No.: WO2011/095270
PCT Pub. Date: Aug. 11, 2011

(65) Prior Publication Data
US 2012/0316367 A1     Dec. 13, 2012

(30) Foreign Application Priority Data
Feb. 4, 2010   (DK) .................................. 2010 00096

(51) Int. Cl.
*C07C 41/09*     (2006.01)
*C07C 43/04*     (2006.01)

(52) U.S. Cl.
CPC .................................... *C07C 41/09* (2013.01)

(58) Field of Classification Search
USPC .......................................................... 568/698
See application file for complete search history.

(56) References Cited

U.S. PATENT DOCUMENTS 4,058,576 A * 11/1977 Chang et al. ................... 585/322
4,778,662 A * 10/1988 Pinto ............................. 422/148

FOREIGN PATENT DOCUMENTS

| | | |
|---|---|---|
| CN | 201180118 Y | 1/2009 |
| GB | 2 046 618 A * | 11/1980 |
| JP | 2004-298768 | 10/2004 |
| JP | 2004298768 A * | 10/2004 |
| JP | 2009149531 A * | 7/2009 |
| SU | 925928 | 5/1982 |
| WO | WO 2006/041253 A1 | 4/2006 |
| WO | WO 2009/078490 | 6/2009 |

* cited by examiner

*Primary Examiner* — Rosalynd Keys
(74) *Attorney, Agent, or Firm* — Dickstein Shapiro LLP

(57) ABSTRACT

Process for the preparation of dimethyl ether comprising the steps of: a) providing a methanol containing feed stock; b) introducing the feed stock into a reaction zone within a gas cooled dimethyl ether reactor and passing the feed stock through the reaction zone; c) introducing a cooling gas stream into a cooling space within the gas cooled dimethyl ether reactor; d) reacting the feed stock in the reaction zone in presence of a catalyst being active in the dehydration of methanol to dimethyl ether to obtain a reactor effluent comprising dimethyl ether.

5 Claims, 1 Drawing Sheet

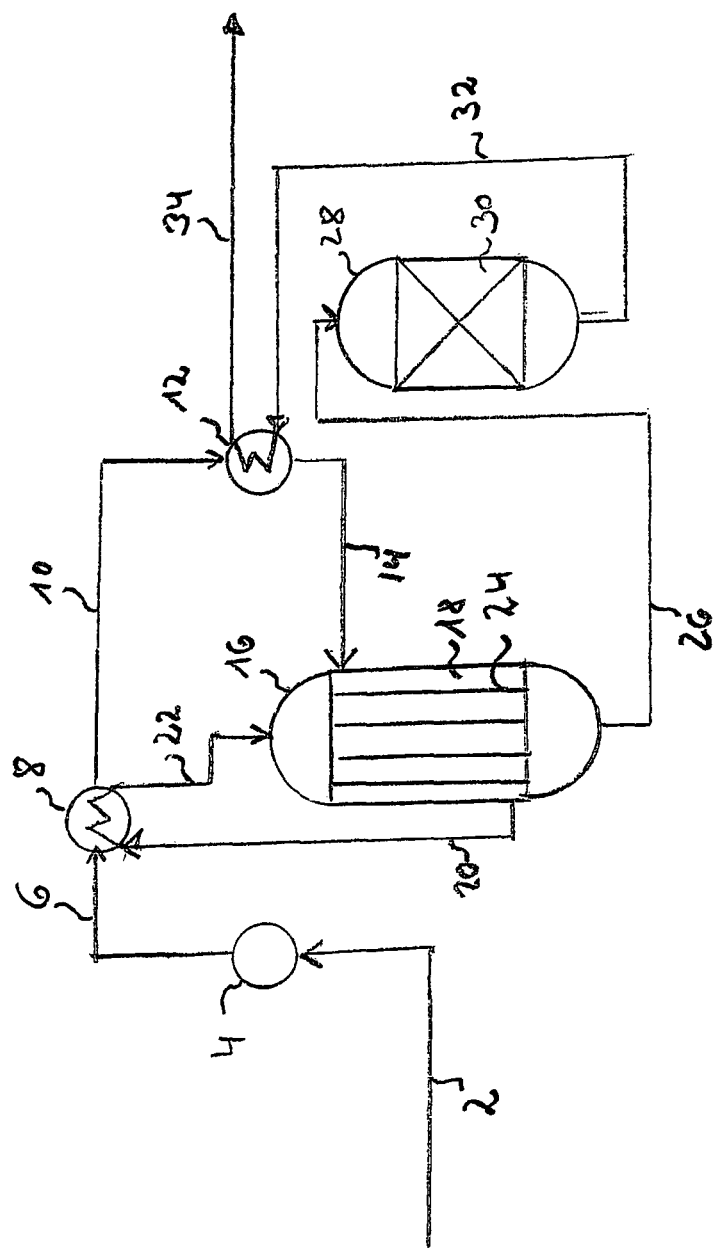

PROCESS FOR THE PREPARATION OF DIMETHYL ETHER

The present invention relates to a process for the preparation of dimethyl ether from a methanol feed stock. In particular, the invention provides catalytic conversion of the methanol feed stock in a gas cooled dimethyl ether reactor by indirect heat exchange with a cooling gas being passed in co-current flow direction with the reacting methanol feed stock through the reactor.

The invention serves to solve the problem with detrimental formation of carbon on the catalyst surface during the dehydration reaction of methanol to dimethyl ether by cooling the reaction to reduce or avoid carbon formation on the catalyst.

Accordingly, this invention is in its broadest embodiment a process for the preparation of dimethyl ether comprising the steps of:
a) providing a methanol containing feed stock;
b) introducing the feed stock into a reaction zone within a gas cooled dimethyl ether reactor and passing the feed stock through the reaction zone;
c) introducing a cooling gas stream into a cooling space within the gas cooled dimethyl ether reactor;
d) reacting the feed stock in the reaction zone in presence of a catalyst being active in the dehydration of methanol to dimethyl ether to obtain a reactor effluent comprising dimethyl ether
e) passing the cooling gas stream through the cooling space in indirect heat exchanging relationship with the feed stock in the reaction zone, wherein flow direction of the cooling gas stream is co-current with the flow direction of the feed stock in the reaction zone.

A useful reactor for use in the inventive process contains within a common shell a plurality of catalyst tubes forming the reaction space. The tubes are arranged spaced apart to leave room for the cooling space. The cooling gas is then introduced on shell side of the catalyst tubes in the cooling space and flows along the shell side in heat exchanging relationship with the reacting gas on tube side of the catalyst tubes. Thereby the reacting gas is cooled below the critical carbon forming temperature.

In further an embodiment of the invention the cooling gas stream being used in the reactor is formed by the methanol feed stock, which after evaporation is introduced into the cooling space of the reactor.

When employing the feed stock as cooling gas stream it is preferred to introduce the stream after having cooled the dehydration reaction into the reaction zone as the feed stock for the methanol dehydration reaction.

In further an embodiment of the invention the methanol feed stock is preheated by indirect heat exchange with the cooling gas stream having been withdrawn from the cooling space prior to introduction into the reaction zone and the pre heated feed stock is further heated with a second hot gas stream prior to introduction into the reaction zone.

In the latter embodiment it is preferred that the second hot gas stream is a reactor effluent from an adiabatic operated catalytic reactor for the conversion of methanol to dimethyl ether.

When employing an adiabatic operated reactor, the feed stock to this reactor is preferably the reactor effluent from the gas cooled dimethyl ether reactor being passed to the adiabatic dimethyl ether reactor for further adiabatically reacting unconverted methanol in the effluent in presence of a catalyst being active in conversion of methanol to dimethyl ether to obtain an adiabatically reacted dimethyl ether reactor effluent.

Catalysts being suitable for use in this invention are per se known in the art and are preferably selected from the group of solid acids, including alumina, alumina silicates or a mixture of these compounds.

The invention is disclosed in more detail by reference to the drawings in which

FIG. 1 shows a simplified flow sheet of a process for the preparation of dimethyl ether in accordance with one embodiment of the invention.

In this embodiment a stream of liquid methanol feed stock is passed in line 2 to an evaporator 4 and evaporated into gaseous form. The gaseous methanol feed stream is then forwarded in line 6 to a first heat exchanger 8.

In the first heat exchanger the gaseous methanol stream is preheated to 220° C. by indirect heat exchange with a hot methanol gas stream 20 having served as cooling gas in gas cooled dimethyl ether reactor 16 as further described below.

The preheated methanol stream is introduced via line 10 into a second heat exchanger 12. In heat exchanger 12 the preheated methanol stream is further heated to 260° C. by indirect heat exchange with a hot dimethyl ether product stream leaving an adiabatically operated dimethyl ether reactor 28 at 336° C.

The thus heated methanol feed stock is subsequently introduced via line 14 at top portion of the gas cooled reactor 16 into cooling space 18. The cooling space is formed between reactor tubes 24 on shell side of the tubes.

When introduced into the cooling space, the gaseous methanol feed stock is employed as cooling gas and is passed in co-current flow direction with the reacting methanol feed stock in tubes 14. The gas cools thereby the methanol dehydration reaction proceeding on the catalyst arranged within tubes 24. Having cooled the reaction by indirect heat exchange, the gaseous methanol feed is withdrawn at a temperature of 320° C. from cooling space 18 at bottom portion of reactor 16 via line 20.

The fed stock having served as cooling gas is subsequently introduced into heat exchanger 8 to preheat the feed stock from line 6 as described above and is thereby cooled to 270° C.

Subsequently the cooled feed stock is passed to reactor 16 in line 22 and introduced at top portion of the reactor into a reaction zone formed by a plurality of catalyst tubes 24.

In the reaction zone methanol in the feed stock is catalytically dehydrated to a gas being rich in dimethyl ether. The reacting feed stock is passed in co-current flow direction with the cooling gas on shell side of the tubes and is thereby cooled by indirect heat exchange with the cooling gas. A reactor effluent being rich in dimethyl ether is withdrawn at 329° C. from bottom portion of the reactor and via line 26 passed to adiabatic reactor 28, optionally after cooling in a heat exchanger (not shown).

Reactor 28 is provided with a fixed bed of a methanol dehydration catalyst 30 and remaining amounts of methanol in the effluent from reactor 16 are adiabatically converted to dimethyl ether.

Prior to a dimethyl ether rich product is collected via line 34, the product is withdrawn from reactor 28 at a temperature of 336° C. and passed via line 32 through heat exchanger 12 for heating the methanol feed stock as described above.

The invention claimed is:
1. Process for the preparation of dimethyl ether comprising the steps of:
a) providing a methanol containing feed stock;
b) introducing the feed stock into a reaction zone within a gas cooled dimethyl ether reactor and passing the feed stock through the reaction zone;

c) introducing a cooling gas stream into a cooling space within the gas cooled dimethyl ether reactor;

d) reacting the feed stock in the reaction zone in presence of a catalyst being active in the dehydration of methanol to dimethyl ether to obtain a reactor effluent comprising dimethyl ether; and e) passing the cooling gas stream through the cooling space in indirect heat exchanging relationship with the feed stock in the reaction zone, wherein flow direction of the cooling gas stream is co-current with the flow direction of the feed stock in the reaction zone;

wherein the cooling gas stream is formed by evaporating the methanol feed stock prior to the introduction into the cooling space, and wherein the cooling gas stream is withdrawn from the cooling space and subsequently introduced as the feed stock into the reaction zone, and wherein the methanol feed stock is preheated in a first heat exchanger by indirect heat exchange with the cooling gas stream having been withdrawn from the cooling space.

2. Process according to claim 1, wherein the methanol feed stock is preheated in the first heat exchanger prior to introduction into the reaction zone and the preheated feed stock is further heated with a second hot gas stream prior to introduction into the reaction zone.

3. Process according to claim 2, wherein the second hot gas stream is a reactor effluent from an adiabatic operated catalytic reactor for the conversion of methanol to dimethyl ether.

4. Process according to claim 1, wherein the reactor effluent obtained in step d) is passed to an adiabatic dimethyl ether reactor, optionally after cooling and adiabatically reacted in the presence of a catalyst being active in conversion of methanol to dimethyl ether to obtain a adiabatically reacted dimethyl ether reactor effluent.

5. Process according to claim 1, wherein the catalyst being active in conversion of methanol to dimethyl ether comprises aluminum and/or alumina silicate.

\* \* \* \* \*